United States Patent
Rasmussen

(10) Patent No.: US 11,276,486 B2
(45) Date of Patent: Mar. 15, 2022

(54) SECURE MOBILE LOCKBOX

(71) Applicant: Mark David Rasmussen, El Cajon, CA (US)

(72) Inventor: Mark David Rasmussen, El Cajon, CA (US)

(*) Notice: Subject to any disclaimer, the term of this patent is extended or adjusted under 35 U.S.C. 154(b) by 204 days.

(21) Appl. No.: 16/777,800

(22) Filed: Jan. 30, 2020

(65) Prior Publication Data
US 2021/0241875 A1 Aug. 5, 2021

(51) Int. Cl.
*G06Q 10/00* (2012.01)
*G16H 20/13* (2018.01)
*G06K 7/10* (2006.01)
*G07C 9/29* (2020.01)
*G06N 20/00* (2019.01)
*G06K 7/14* (2006.01)
*G06Q 10/08* (2012.01)

(52) U.S. Cl.
CPC ......... *G16H 20/13* (2018.01); *G06K 7/10297* (2013.01); *G06K 7/10366* (2013.01); *G06K 7/1413* (2013.01); *G06N 20/00* (2019.01); *G06Q 10/087* (2013.01); *G07C 9/29* (2020.01)

(58) Field of Classification Search
CPC . G16H 20/13; G06N 7/06; G07C 9/29; G06K 7/10297
USPC .......................................................... 705/2
See application file for complete search history.

(56) References Cited

U.S. PATENT DOCUMENTS

| | | | |
|---|---|---|---|
| 7,299,981 B2 | 11/2007 | Hickle et al. | |
| 9,082,236 B2 | 7/2015 | Shoenfeld | |
| 10,007,764 B2 | 6/2018 | Kim | |
| 2012/0130534 A1* | 5/2012 | Wurm | G07F 17/0092 700/236 |
| 2014/0262690 A1 | 9/2014 | Henderson et al. | |
| 2014/0326744 A1 | 11/2014 | Ratnakar | |
| 2018/0091782 A1* | 3/2018 | Bashkin | G07C 9/00563 |
| 2018/0240541 A1 | 8/2018 | Ervin et al. | |
| 2019/0057566 A1 | 2/2019 | Mlynarczyk et al. | |
| 2019/0308819 A1 | 10/2019 | Greyshock | |

(Continued)

FOREIGN PATENT DOCUMENTS

WO 2007101840 A1 9/2007

*Primary Examiner* — Ahshik Kim
(74) *Attorney, Agent, or Firm* — Pablo Meles

(57) ABSTRACT

A system and method for holding, transporting, and tracking electronically tagged objects maintained in a portable carrier housing includes a locking mechanism for enabling limited authorized access using a proximity sensor recognizing an identity code of an authorized user, a location tracker for detecting the location of the portable carrier, and an inventory logger registering placement and removal of the electronically tagged objects within and out of the portable carrier housing, registering the location of the portable carrier housing at a time of placement or removal of the electronically tagged object, and registering the identity code of the authorized user within proximity of the proximity sensor. The system further includes a transmitter for uploading data from the inventory logger to a database and a receiver for at least receiving instructions for locking the portable carrier housing when detecting an attempted unauthorized access or detecting a condition indicative of unauthorized access.

20 Claims, 7 Drawing Sheets

(56) References Cited

U.S. PATENT DOCUMENTS

2019/0378602 A1* 12/2019 LaTorraca ............ G06Q 10/087
2021/0131164 A1* 5/2021 Tulsidas ............. G07C 9/00912

* cited by examiner

200

SECURE MOBILE LOCKBOX

BACKGROUND

Field of the Invention

The present disclosure is directed to a method and system for securely and safely holding, transporting, and tracking electronically tagged objects and more particularly in some embodiments to a method and system for managing and dispensing controlled medications for use in an operating room, surgery center, doctor's office, or other suitable environment.

Description of the Related Art

Current methods to address some of the issues resolved by the current embodiments use a large stationary device to secure medications or rely on insecure storage containers to transfer mediations to locked cabinets or carts and/or fail to account for scheduled dispensing or geographically restricted dispensing of controlled medications. Current methods also continue to allow unauthorized users to circumvent existing security measures or allow authorized users to abuse, pilfer or divert the contents of the electronically tagged objects.

DETAILED DESCRIPTION

Figure 1:
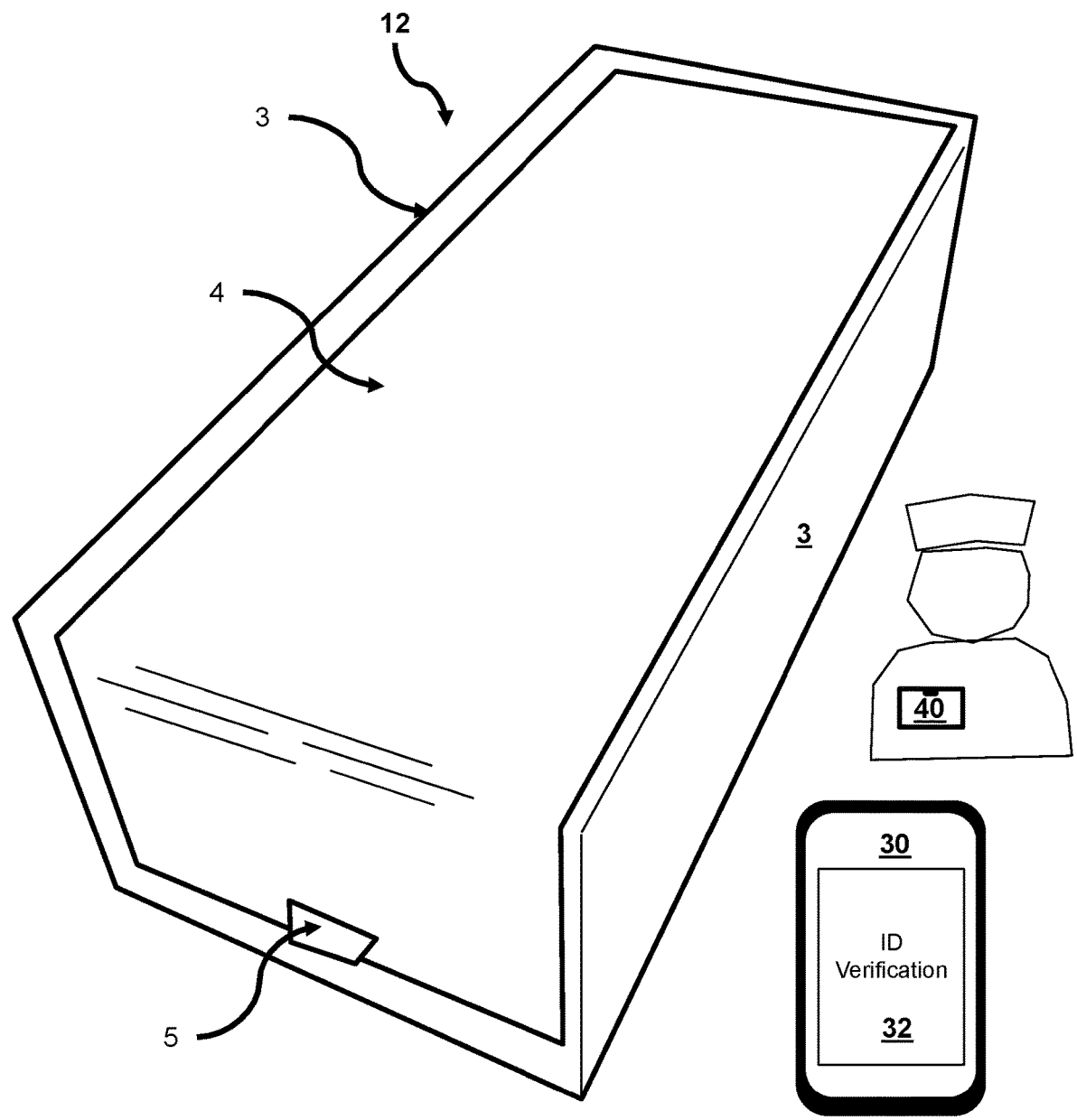
FIG. 1 illustrates a system for holding, transporting, and tracking electronically tagged objects in a portable carrier housing or lock box in accordance with the embodiments.

In some embodiments, a system for holding, transporting, and tracking electronically tagged objects maintained in a portable carrier housing can include a locking mechanism for enabling limited authorized access to the portable carrier housing using a proximity sensor recognizing an identity code of an authorized user where the portable carrier housing goes to an unlocked status when the proximity sensor detects the identity code of the authorized user and returns to a locked status when the proximity sensor fails to detect the identity code of the authorized user. The system can further include a location tracker coupled the portable carrier for detecting the location of the portable carrier at least when the locking mechanism changes status from the locked status to the unlocked status or when the locking mechanism changes from the unlocked status to the locked status, and an inventory logger registering placement and removal of the electronically tagged objects within and out of the portable carrier housing or within slots or specific areas of the portable carrier housing, registering the location of the portable carrier housing at a time of placement or removal of the electronically tagged object, and registering the identity code of the authorized user within proximity of the proximity sensor causing the locking mechanism to provide limited authorized access. In some embodiments, the system can manage access to the portable carrier housing based on a scheduled dispensing routine and/or permitted or authorized dispensing locations. The system can further include a transmitter for uploading data from the inventory logger to a database and a receiver for at least receiving instructions for remotely locking the portable carrier housing when detecting an attempted unauthorized access or detecting a condition indicative of unauthorized access which can be based on identity, location, scheduling or any combination thereof.

In some embodiments the proximity sensor of the system uses a Radio Frequency Identification (RFID) tag or a Near Field Communication (NFC) device. In some embodiments, the electronically tagged objects use Radio Frequency Identification (RFID) tags or alternatively use Radio Frequency Identification (RFID) tags and barcodes. In some embodiments, the electronically tagged objects are vials of medicine or syringes. In yet other embodiments, the electronically tagged objects can be one or more objects selected among keys, firearms, ammunition, or medicine and the embodiments are not necessarily restricted to such objects. In some embodiments, the locking mechanism is a biometric access system selected among a fingerprint reader, a facial recognition reader, an iris scanner, or a voice recognition reader or any combination thereof. In some embodiments, the identity code is stored in a mobile phone of the authorized user. In some embodiments, the system further includes a processor configured to acknowledge the receipt of a temporary grant access code from the authorized user to a third party enabling temporary access by the third party to the portable carrier housing.

In some embodiments, the portable carrier housing further includes a vial registration system using slots within the portable carrier housing and where the vial registration system uses one or more among magnetism, barcodes, or mechanical registration to register the placement or removal of vials within the portable carrier housing or to register the placement or removal of vials within a particular slot of the portable carrier housing. In some embodiments, the portable carrier housing further includes at least one scale that automatically weighs the electronically tagged object upon insertion into the portable carrier housing. In some embodiments, the location tracker includes one or more among a GPS device, a beacon-reading device, a camera, or any combination thereof. In some embodiments, the system registers transfers of electronically tagged objects from a main storage site to the portable carrier housing. In some embodiments, the system registers inventory data at a first time in a day when electronically tagged objects are transferred from a main storage site to the portable carrier housing and registers inventory data at a second time in the day when the portable carrier housing is returned to the main storage site.

In some embodiments, the system can further include a cart for carrying the portable carrier housing and where the cart includes a power-charging source for charging rechargeable batteries stored within the portable carrier housing. In some embodiments, the portable carrier housing can include a modular carrying component enabling different configurations for carrying different shapes or amounts of the electronically tagged objects.

In some embodiments, a system for holding, transporting, and tracking electronically tagged medicine containers maintained in a portable carrier housing can include a locking mechanism for enabling limited authorized access to the portable carrier housing using an identity code representative of an authorized user, a location tracker coupled the portable carrier for enabling limited authorized access to the portable carrier housing using an identity code representative of an authorized user, and an inventory logger registering placement and removal of the electronically tagged medicines within and out of the portable carrier housing, registering the location of the portable carrier housing at a time of placement or removal of the electronically tagged medicine, and registering the identity code of the authorized user when placing or removing the electronically tagged medicines. The system can further include a transmitter for uploading data from the inventory logger to a database and a receiver for at least receiving instructions for remotely locking the portable carrier housing when detecting an attempted unauthorized access or detecting a condition indicative of an attempted authorized access. Such conditions indicative of unauthorized or authorized access can be based on identity code, scheduling, and/or location or other factors that can be programmatically configured and optionally further use artificial intelligence or machine learning more particularly to more adequately reflect real world conditions as a system is utilized in a particular environment and eventually across a number of different environments. In some embodiments, the locking mechanism uses a proximity sensor and the portable carrier housing goes to an unlocked status when the proximity sensor detects the identity code of the authorized user and returns to a locked status when the proximity sensor fails to detect the identity code of the authorized user.

In some embodiments, a system for holding, transporting, and tracking electronically tagged medicine containers maintained in a portable carrier housing can include a locking mechanism for locking and unlocking access to the portable carrier housing, a transceiver, a memory having computer instructions stored therein, and one or more processors operatively coupled to the memory, transceiver, and locking mechanism. The one or more processor when executing the computer instructions, performs the functions of enabling limited authorized access to the portable carrier housing using an identity code representative of an authorized user using the locking mechanism, enabling limited authorized access to the portable carrier housing using an identity code representative of an authorized user using a location tracking device, registering placement and removal of the electronically tagged medicines within and out of the portable carrier housing, registering the location of the portable carrier housing at a time of placement or removal of the electronically tagged medicine, registering the identity code of the authorized user when placing or removing the electronically tagged medicines using an inventory logger, uploading data using the transceiver from the inventory logger to a database, and receiving instructions using the transceiver for remotely locking the portable carrier housing when detecting an attempted unauthorized access or detecting a condition indicative of an attempted authorized access.

In some embodiments, a smart portable box provides storage for controlled substances such as narcotics or anxiolytics for use by anesthesiologists, Certified Registered Nurse Anesthetists (CRNAs), or sedation nurses. Appropriate authorized personnel obtain access to these medications via electronic locks that can only be unlocked by such authorized individuals when located in authorized locations. Contents of the box can be inventoried and accounted for with an electronic chain of custody.

The securing and tracking of controlled substances in a healthcare setting or institution is an essential task that cannot be ignored. Failure to adequately secure narcotics and anxiolytics can result in diversion and liability for the institution. Larger facilities with resources typically install stationary medication access machines that require passwords and biometric interaction to issue medications to doctors or nurses for patient administration. Smaller facilities such as ambulatory surgery centers often rely on methods involving locked cabinets and carts along with small containers and documentation to ensure compliance with proper narcotic guidelines. Often this presents a suboptimal method that is vulnerable to diversion and increases an administrative burden to track those medications. Diversion presents a danger to staff and patients and methods and devices that pose a barrier such as those presented herein are a welcome addition to the healthcare environment. Any reduction in paperwork and administrative burden is also preferred. In the proposed embodiments, the device and methods disclosed alleviate some of those burdens and makes medication delivery safer and more accountable. A smart portable box as contemplated can also help reduce costs for smaller facilities looking to secure their narcotics or other items in comparison to fixed solutions or methods that typically have higher upfront costs in construction and materials. A smart portable box can also be utilized in conjunction with only fixed methods and could reduce overall costs in a system.

Referring to FIGS. 1-4, a system 10 for holding, transporting, and tracking electronically tagged objects (42 and/or 48) maintained in a portable carrier housing 12 can include a locking mechanism (2G) for enabling limited authorized access to the portable carrier housing 12 using a proximity sensor (2B) recognizing an identity code of an authorized user where the portable carrier housing goes to an unlocked status when the proximity sensor detects the identity code of the authorized user and returns to a locked status when the proximity sensor fails to detect the identity code of the authorized user. The system can further include a location tracker (2D) coupled the portable carrier for detecting the location of the portable carrier at least when the locking mechanism changes status from the locked status to the unlocked status or when the locking mechanism changes from the unlocked status to the locked status, and an inventory logger (2C) registering placement and removal of the electronically tagged objects within and out of the portable carrier housing, registering the location of the portable carrier housing at a time of placement or removal of the electronically tagged object, and registering the identity code of the authorized user within proximity of the proximity sensor causing the locking mechanism to provide limited authorized access. The system can further include a transmitter (2F) for uploading data from the inventory logger to a database (see 60C or 69 in FIG. 6) and a receiver (2F) for at least receiving instructions for remotely locking the portable carrier housing when detecting an attempted unauthorized access or detecting a condition indicative of unauthorized access. In some embodiments, the condition indicative of unauthorized access can be based not only on recognizing an authorized user, but further optionally based on a known schedule of dispensing or dispensing routine and/or permitted or authorized dispensing locations.

Construction of the portable carrier housing or lockbox 12 can take many forms, but as shown in the system 10 of FIG. 1, the lockbox 12 can simply include an outer housing 3, a lid 4 for selectively securing the lockbox 12, and the associated electronics, sensors and locking mechanism(s) to implement the embodiments as further detailed below with respect to FIG. 2. In FIG. 1, the lockbox 12 is shown in a closed or locked mode. In one embodiment, the lid 4 can be coupled to the outer housing 3 via a hinge and can further include a handle 5 to facilitate the opening and closing of the lockbox 12. In one simple arrangement, the lockbox 12 can remain in a locked mode until a proximity sensor detects a badge 40 associated with an authorized user or a phone ID 32 from a phone associated with an authorized user or a combination of both. In some embodiments, the lockbox 12 can remain in a locked mode until a proximity sensor detects an authorized user and further until the lockbox 12 coincides with a given dispensing schedule and/or with an authorized dispensing location.

Figure 2:
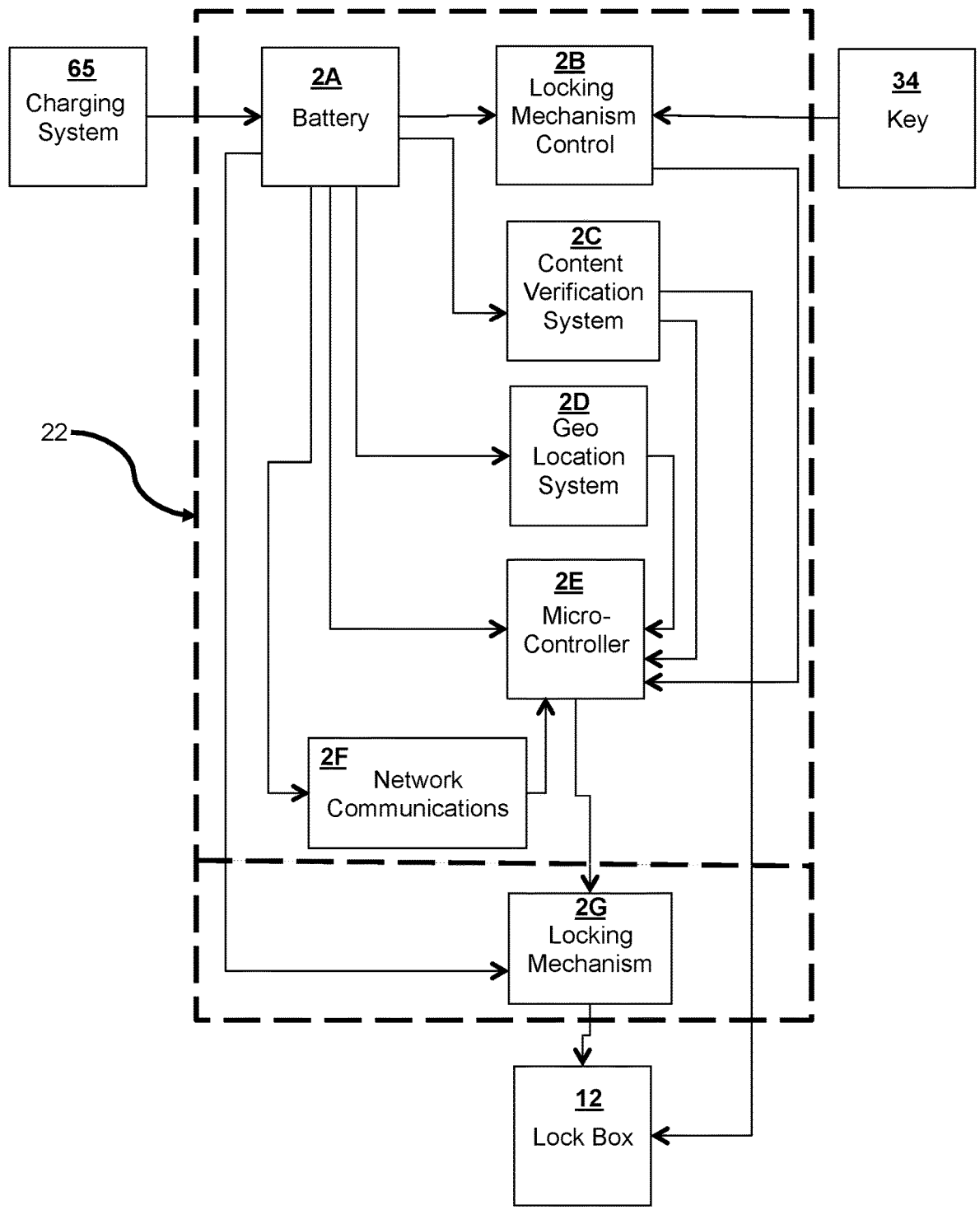
FIG. 2 illustrates a block diagram of a system for holding, transporting and tracking electronically tagged objects in accordance with the embodiments.

Referring to FIG. 2, a system 20 can include the lockbox 12, the associated electronics and sensor module 22, a charging system 65, and a key 34. The module 22 can include a locking mechanism 2G, but the locking mechanism can be implemented outside the module 22 or as a separate part of the lock box 12. In some embodiments as shown in FIG. 2, the module 22 can include a battery 2A that powers the various coupled components of the module 22 including a locking mechanism control 2B, a content verification system 2C, a geo location system 2D, a microcontroller 2E, a network communications module 2F, and the locking mechanism 2G. The battery 2A can be any power source such as a rechargeable battery.

Operationally, the locking mechanism control 2B can include a proximity sensor for detecting a key 34 within a predetermined distance from the lockbox 12. The locking mechanism control 2B can be implements in any number of ways including the use of a Radio Frequency Identification (RFID) tag or a Near Field Communication (NFC) device that interacts with or utilizes the key.

In some embodiments, the locking mechanism 2G and/or locking mechanism control 2B includes a biometric access system selected among a fingerprint reader, a facial recognition reader, an iris scanner, or a voice recognition reader or any combination thereof. In some embodiments, the locking mechanism can further include a keypad to allow a user to physically enter a pin number or a voice-to-text system to allow a user to audibly enter a catch phrase or a pin number. In some embodiments, the identity code is stored in a mobile phone of the authorized user that can be used alone as a means of unlocking the lockbox 12 or in combination with other biometric devices or authenticating mechanisms. The key 34 and locking mechanism control 2B can include a synchronized pseudo-random number generator to allow for further enhanced security. In some embodiments, the key 34 and locking mechanism control 2B can utilize PKI or SSL certificates as part of the security measures. In some embodiments, the system 20 can further include a processor (such as microcontroller 2E) configured to acknowledge the receipt of a temporary grant access code from the authorized user to a third party enabling temporary access by the third party to the portable carrier housing.

Figure 3:
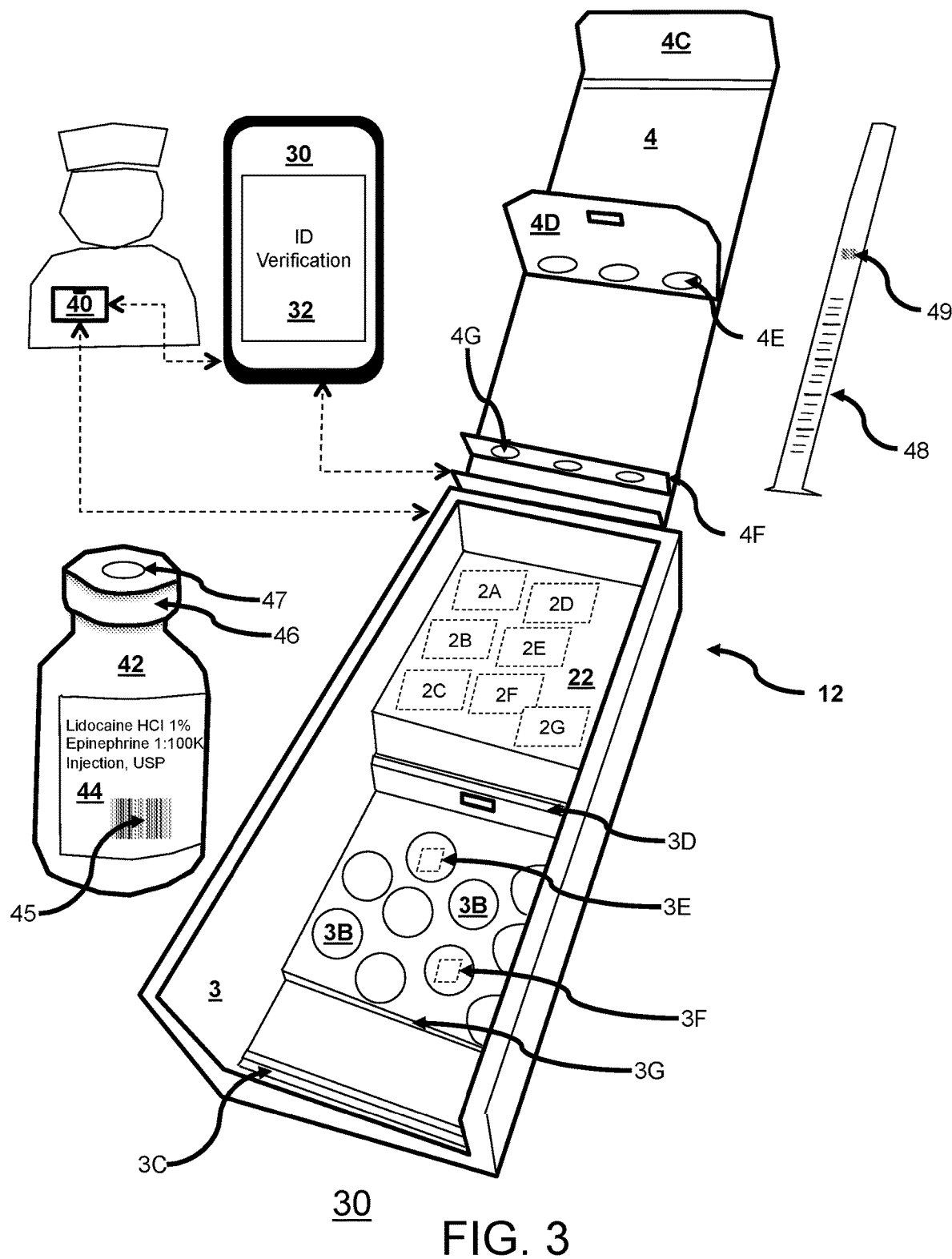
FIG. 3 is a representation of the system of FIG. 1 including a portable carrier housing in an open mode before stocking or filling the housing with electronically tagged objects into vial slots or other storage areas of the portable carrier housing in accordance with the embodiments.

In some embodiments and further referring to FIG. 3, the electronically tagged objects 42 or 48 can use barcodes (45 or 49 respectively) or use Radio Frequency Identification (RFID) tags or alternatively use both Radio Frequency Identification (RFID) tags and barcodes. In some embodiments, the electronically tagged objects are vials of medicine or syringes. In yet other embodiments, the electronically tagged objects can be one or more objects selected among keys, firearms, ammunition, or medicine and the scope of the embodiments are not intended to be limited to such items. The content verification system 2C would include suitable sensors for detecting the insertion and removal of such electronically tagged objects into and out of the lockbox 12. In some embodiments, the content verification system 2C can include a vial registration system 3E using slots (3B of FIG. 3 or 4) within the portable carrier housing 12 and where the vial registration system uses one or more among magnetism, barcodes, or mechanical registration to register the placement or removal of vials within the portable carrier housing or to register the placement or removal of vials within a particular slot of the portable carrier housing. In some embodiments, the portable carrier housing further includes a vial registration system 3F in the form of at least one scale that automatically weighs the electronically tagged object upon insertion into the portable carrier housing 12 or into the slot 3B of the portable carrier housing or lockbox 12. The content verification system 2C can be embodied in many different structures including, but not limited to a camera such as a camera having a scanning, wide angle, or fisheye lens, or a scale or weighing device. In other arrangements, the tagged objects could use magnetism to evidence their presence in a slot. Using a scale or weighing device can confirm the expected weight of the (unused) contents and provides additional corroboration that another substance has not been substituted for the original contents of a vial or other container.

In some embodiments, the portable carrier housing can include a modular carrying component 3G enabling different configurations for carrying different shapes or amounts of the electronically tagged objects. If the vials are of different sizes or shapes or of a different number, a different modular carrying component 3G in the form of a removal tray can replace the existing modular carrying components so that the new sizes, shapes or numbers of electronically tagged objects can be appropriately accommodated.

In some embodiments, the location tracker 2D includes one or more among a GPS device, a beacon-reading device, a camera, or any combination thereof to enable the tracking and registration of the location of the lockbox 12. In some embodiments, the location of the lockbox 12 can be registered and tracked periodically or selectively upon events such the opening and closing of the box or upon detection of movement of the box using a motion sensor such as an accelerometer. If a camera is used for location, the camera can register locations via identification of objects, barcodes, text recognition, or any combination thereof.

With reference again to the system 30 of FIG. 3, the system is shown with the lockbox 12 before being provisioned with electronically tagged objects 42 and 48. The lockbox 12 is placed in an open or unlocked mode since the locking mechanism control 2B in the form of a proximity sensor (in conjunction with the microcontroller 2E) can detect the proximity of a tag, a badge or card 40 and/or a smart phone 30 with ID verification 32 having the appropriate authenticated key 34. The "key" 34 can be detected wirelessly using any number of alternative wireless protocols or the key 34 can be a combination of wireless and wired authentication schemes using biometrics on the lockbox 12 itself or on a wireless device such as the smartphone 30 or a combination of both. In some embodiments, the key for authorized access can be obtained using just the badge 40 alone, or just the ID verification on a smartphone or other wireless device, or via facial recognition alone or any combination thereof. Once an authorized person using a "key" 34 initially opens the lockbox 12, the lockbox can be provisioned with electronically tagged objects 42 and 48 such as the vial and syringe shown. For example, the vial 42 can include a label 44 with the barcode 45 and/or a lid 46 with an RFID tag 47. As the vial 42 is inserted in a slot 3B of the lockbox 12, the system using the content verification system 2C and the vial registration system 3E working with the slots 3B registers the placement of the vials within the portable carrier housing and can even register the placement or removal of vials within a particular slot of the portable carrier housing if desired. In some embodiments, the vial registration system 3F can come in the form of at least one scale that automatically weighs the electronically tagged object upon insertion into the portable carrier housing 12 or into the slot 3B of the portable carrier housing or lockbox 12. The scale (3F) can register the weight of a particular narcotic and confirm that the contents has not been tampered or changed since the weight should remain the same if unused. The RFID 47 can also assist in determining if there has been tampering with the vial as the vial can optionally come with an RFID that is associated with the lid and can change upon alteration of the lid 46. In another example, the syringe 49 can include a barcode 49 directly printed on the tube of the syringe 49 and the content verification system 2C can use a sensor such as a bar code scanner to determine placement or removal of the vial. Note that the content verification system 2C is intended to reduce the use of paper tracking and enable an automatic inventorying system.

Also note that the embodiments herein contemplate multi-modal authentication, but certain "keys" alone or in combination are more suitable in an operating room setting. In a setting where gloves and masks are frequently used, a fingerprint reader and facial recognition might not be completely suitable and other alternatives such as voice authentication or badges with NFC or RFID might be best utilized alone or in combination with other biometrics that is more compatible in an environment where gloves and masks are used by the authorized user.

Figure 4:
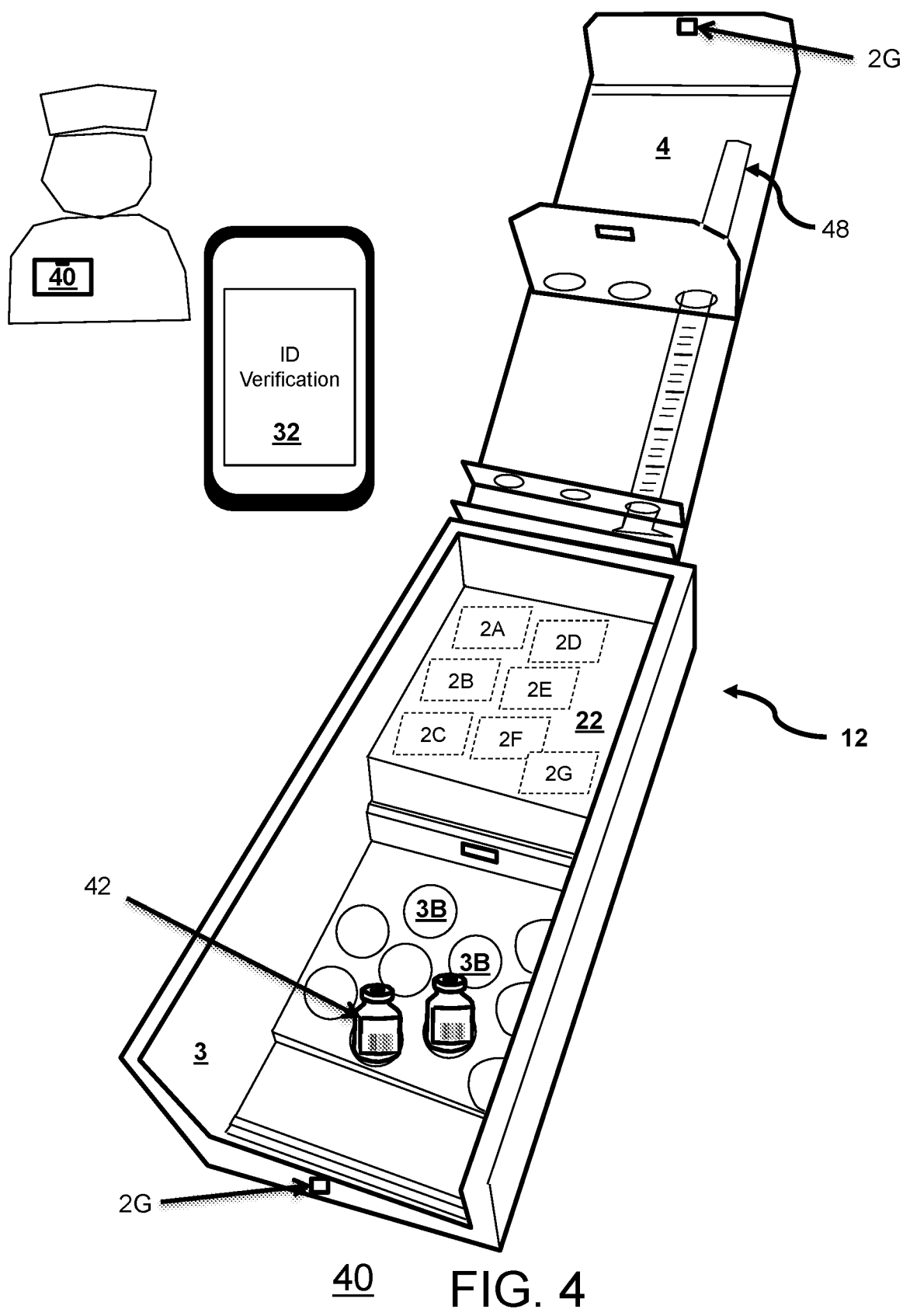
FIG. 4 is a representation of the system of FIG. 1 including the portable carrier housing in an open mode after stocking or filling the housing with electronically tagged objects into vial slots or other storage areas in accordance with the embodiments.

Referring to FIG. 4, a system 40 similar to the system 30 illustrates the lockbox or portable carrier housing 12 provisioned with the electronically tagged objects such as the vials 42 and the syringe 48. The system 40 via the locking mechanism control 2B, the content registration system 2C, and the microcontroller 2E can track and register the contents of the lockbox 12 and further identify who accessed and provisioned the lockbox 12.

In some embodiments, the system registers transfers of electronically tagged objects from a main storage site to the portable carrier housing. In some embodiments, the system registers inventory data a first time in a day when electronically tagged objects are transferred from a main storage site to the portable carrier housing and registers inventory data a second time in the day when portable carrier housing is returned to the main storage site.

The lockbox 12 can be programmed in any number of ways in terms of authentication, lock control mechanism, and content verification among other operations. The programming will obviously depend on the environment and available device resources. Referring to the flow chart in FIG. 5, a method 50 illustrates one of many ways that the lockbox 12 can be programmed in accordance with the embodiments. In the context of a clinic, hospital, or surgical facility using sedation or anesthesia as the electronically tagged objects and an anesthesia nurse and anesthesiologist as the authorized personnel, the method 50 can begin at step 51 and move to a morning controlled medication count and log at step 51A that can make a comparison with a count and log from a prior time such as a prior evening. Supposedly the count and log from a prior evening count and log to a following morning count and log should remain unchanged if the lockbox 12 remained secure and no diversion occurred. The morning count and log at step 51A can be further updated if the lockbox 12 is being further provisioned in the morning with additional medications. At decision block 51B, a determination is made whether the count is correct. If the count is incorrect at decision block 51B, an alert can be provided to facilitate an administrative review at step 52. If the count is correct at decision block 51B, then the method 50 can continue with controlled medication distribution (throughout a particular day) to the authorized personnel such as the physician or anesthesiologist at step 53. The method 50 can continue with the sedation and anesthesia being dispensed to the patient at step 54 before a surgical procedure at step 55 and the subsequent return of unused medications at step 56. Once the day is over and all surgical procedures are done for the day, the method 50 can include an evening controlled medication count and log at step 57. If the count is incorrect at decision block 57A, then an alert can be provided to facilitate the administrative review at step 52. If the count is correct at decision block 57, the method is completed at step 58. In some embodiments, the method 50 can include additional confirmations throughout the day to determine if the count is correct. For example, the method can return to decision block 51B after step 53 and/or after step 56 for additional tracking throughout a day. Steps 53 and 56 (and other steps) can coincide with the event of the lockbox 12 being opened or closed by authorized personnel or when the lockbox 12 is opened in an unauthorized manner or outside a predetermined schedule or outside an authorized area.

Figure 6:
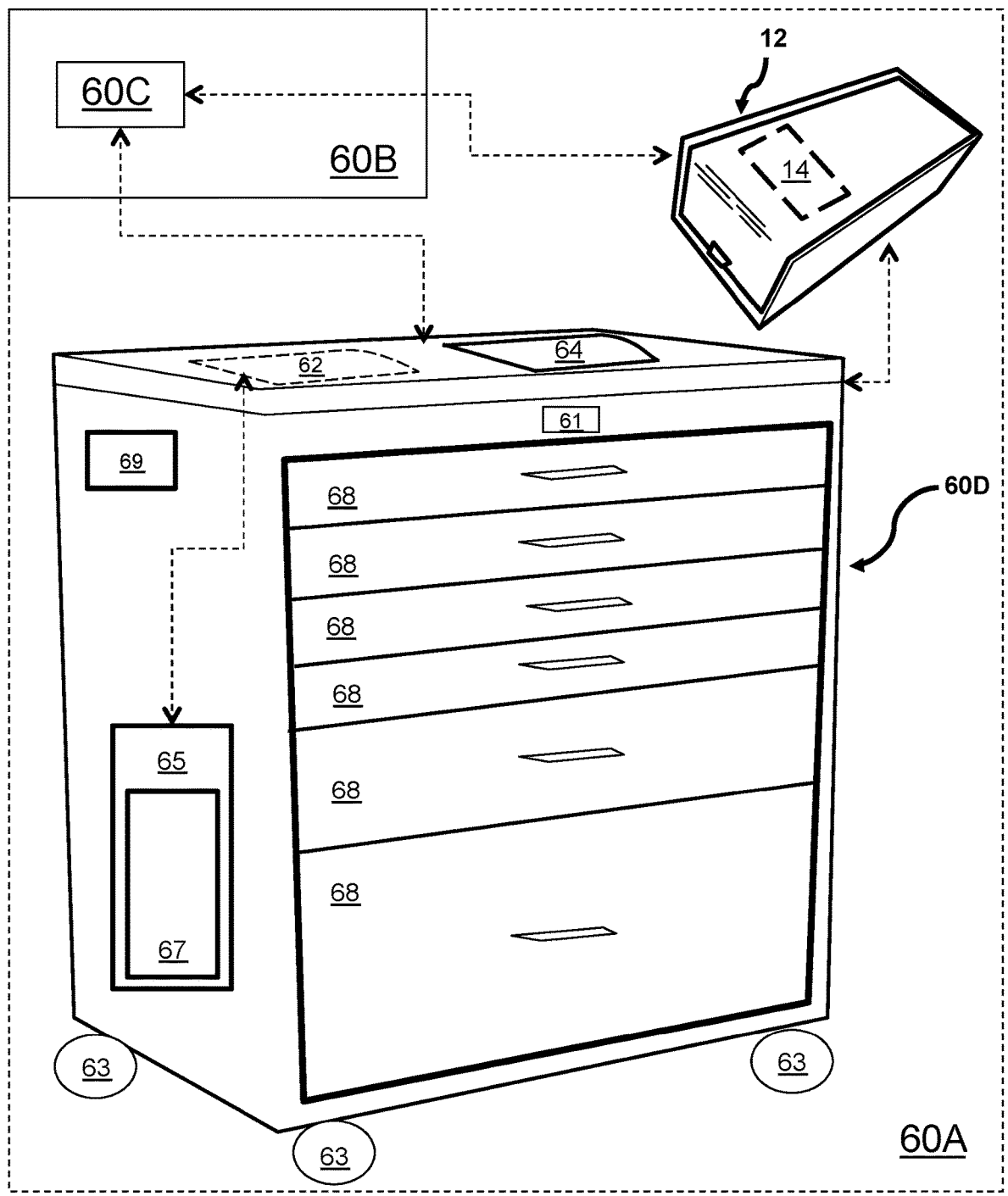
FIG. 6 illustrates the system of FIG. 1 and further represents an anesthesia cart and optional charging system used in conjunction with the portable carrier housing in accordance with the embodiments.

In some embodiments and with further reference to a system 60 of FIG. 6, the system can further include a cart 60D for carrying the portable carrier housing 12 and where the cart includes a power-charging source 67 for charging rechargeable batteries (2A) stored within the portable carrier housing 12. The cart 60D is shown within the context of a facility 60A such as a hospital, clinic or surgical center and further optionally including a storage room 60B within the facility 60A with secure main storage 60C such as a cabinet. The cart 60D can include a number of drawers 68 that can be locked via a locking mechanism 61 which can simply be a mechanical lock or a locking mechanism similar to the locking mechanism and locking mechanism control used on the lockbox 12. The cart 60D can be moved around facilitated by the use of wheels or casters 63. The cart 60D can further include a power charging system 65 that includes the power-charging source 67. The power charging system 65 can be coupled to a charging pad 62 that can either have actual contacts or can alternatively use inductive charging to charge the battery 2B within the lockbox 12 when the lockbox 12 is placed upon or in close proximity of the charging pad 62. The cart can further include a user interface such as a video screen 64 to enable the authorized users to determine the status of one or more conditions relating to the cart 60D and/or lockbox 12 and/or the main storage 60C. Such conditions can include respectively verified authentication status, locked or unlocked status, location, and medicine count and log. Depending on the personnel, more or less information can be provided. An administrator would presumably have full access to all information whereas a nurse or other personnel may have less. Further note that the lockbox 12 can also be optionally configured to include a user interface such as a LCD or video screen 14 to enable access to similar information.

The cart can further include a module 69 that can include similar components found in the module 22 of the lockbox 12. The module 69 as well as module 22 (as part of the content verification system 3C) and main storage 60C can include a synchronized database that enables the corroborated and synchronized count of electronically tagged objects via wireless communication. Thus, the lockbox 12 can communicate with the cart 60D and the main storage 60C, the cart 60D can communicate with the lockbox 12 and the main storage 60C, and the main storage 60C can communication with the lockbox 12 and the cart 60D as is necessary for providing the synchronized count and log.

In some embodiments, a system 40 for holding, transporting, and tracking electronically tagged medicine containers 42 as (shown in FIG. 4) maintained in a portable carrier housing 12 can include a locking mechanism 2G such as an electromagnetically enabled lock for enabling limited authorized access to the portable carrier housing 12 using an identity code representative of an authorized user, a location tracker 2D coupled the portable carrier 12 for enabling limited authorized access to the portable carrier housing using an identity code representative of an authorized user, and an inventory logger 2C registering placement and removal of the electronically tagged medicines within and out of the portable carrier housing 12, registering the location of the portable carrier housing 12 at a time of placement or removal of the electronically tagged medicine 42, and registering the identity code of the authorized user when placing or removing the electronically tagged medicines. Thus, a data record can include one or more of a timestamp of an event, an identity code of an individual associated with the event, a count of electronically tagged objects and possibly a measured count of the contents of the electronically tagged objects. In some embodiments, the data record can further include location information such as the location of the portable carrier 12 at the time of the event. The system can further include a transmitter 2F for uploading data from the inventory logger 2C to a local or remote database and a receiver (also part of 2F) for at least receiving instructions for remotely locking the portable carrier housing when detecting an attempted unauthorized access or detecting a condition indicative of an attempted authorized access. In some embodiments, the locking mechanism uses a proximity sensor 2B and the portable carrier housing 12 goes to an unlocked status when the proximity sensor 2B detects the identity code of the authorized user within a given proximity and returns to a locked status when the proximity sensor fails to detect the identity code of the authorized user within the given proximity. Note that the lid can include a spring-loaded hinge or other mechanism that can be biased to selectively return the lid to a closed position upon a given or programmed instruction. For example, if the lid is left open for a predetermined time period without an authorized user within proximity, the spring-loaded hinge or biasing mechanism can be selectively activated to cause the lid to automatically close and place the lockbox 12 in a locked mode. Similarly, if the lid is left physically closed, but unlocked or in an unlocked mode for a predetermined time period without an authorized user within proximity, software or other mechanisms can be implemented to place the system or portable carrier or lockbox 12 in a locked mode after the predetermined timer period passes in order to reduce the opportunities for unauthorized access.

Figure 7:
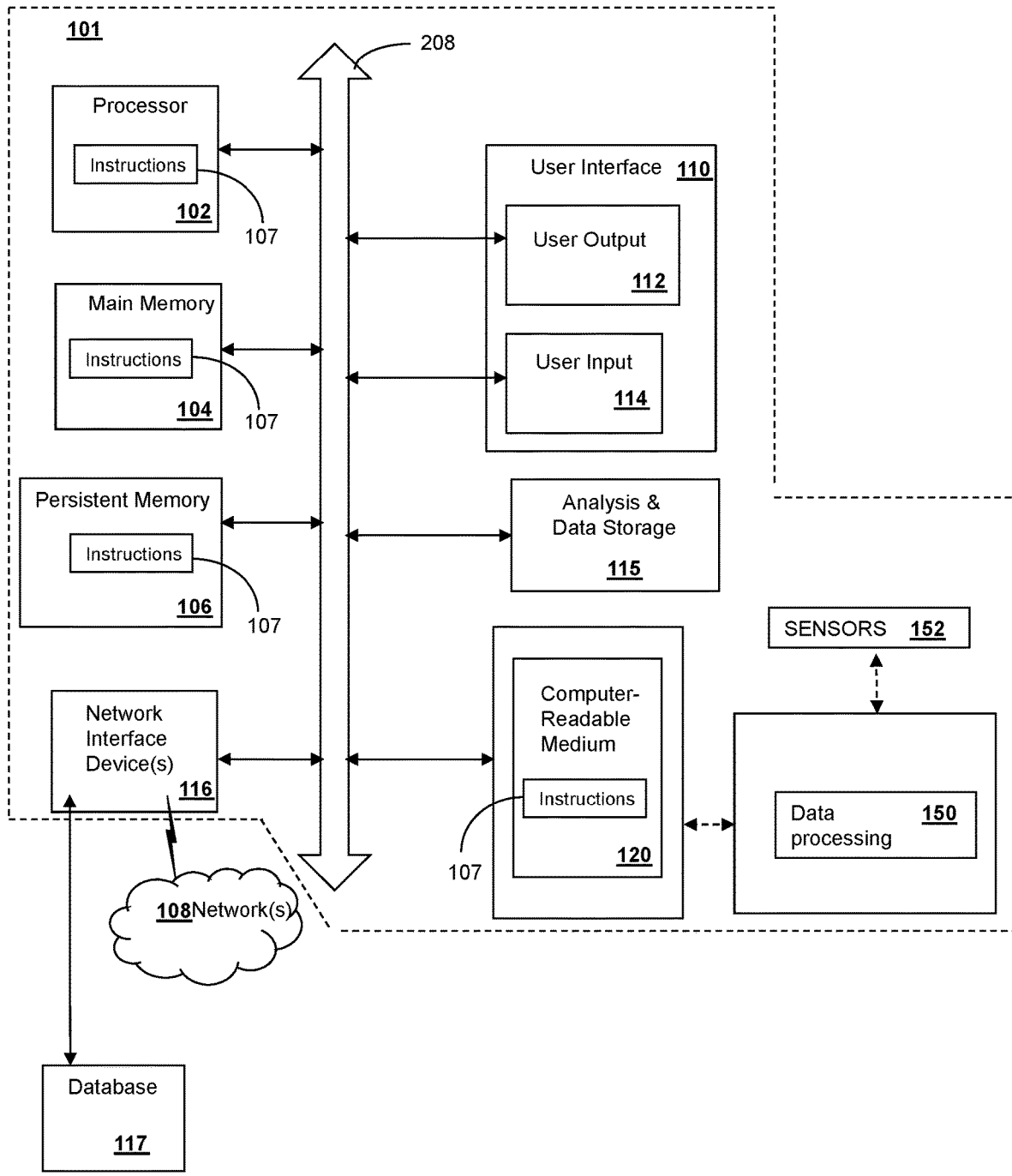
FIG. 7 is a block diagram of a system in accordance with the embodiments.

In some embodiments, and with further references to FIG. 7, a system 200 for holding, transporting, and tracking electronically tagged medicine containers maintained in a portable carrier housing 12 can include any number and combination of the previously described components above as well as one or more processors which when executing the computer instructions, performs the functions of enabling limited authorized access to the portable carrier housing 12 using an identity code representative of an authorized user using the locking mechanism, registering placement and removal of the electronically tagged medicines within and out of the portable carrier housing, registering the location of the portable carrier housing at a time of placement or removal of the electronically tagged medicine, and registering the identity code of the authorized user when placing or removing the electronically tagged medicines using an inventory logger, uploading data using the transceiver from the inventory logger to a database, and receiving instructions using the transceiver for remotely locking the portable carrier housing when detecting an attempted unauthorized access or detecting a condition indicative of an attempted unauthorized access.

In some embodiments, the system can utilize artificial intelligence and more particularly machine learning which can use exemplary training data and/or actual commercial use data to further refine what is intended to serve as "conditions indicative of unauthorized or authorized access" based on a particular environment or a number of known environments. Machine learning is a method of data analysis that automates analytical model building. It is a branch of artificial intelligence based on the idea that systems can learn from data, identify patterns and make decisions with minimal human intervention. Some of the training data that can be used to help identify patterns and make decisions can include fields such as identity codes, scheduling data, location data and/or other parameters obtained from sensors such as cameras, video monitoring devices, audio devices, temperature or other sensor data that can be programmatically configured to more adequately and accurately reflect real world conditions as a system is utilized in a particular environment and hopefully across different environments. Ideally, using machine learning enables systems to automatically learn and improve from experience without being explicitly programmed. Machine learning in the embodiments herein can focus on the development of computer programs (using the Python programming language, for example) to access data and use it to learn for itself in order to better predict when a lockbox should be in either a locked or an unlocked mode.

One embodiment of this method and process is a smart container, lockbox or portable carrier housing that can be transported by hand from operating room to operating room. The smart container fits on top of an anesthesia cart or inside one of the drawers. The smart container has sufficient free space to accommodate vials and syringes for multiple patients. The portability and data logging of this smart container offers multiple advantages over current methods and systems.

An anesthesiologist may be required to move from operating room to operating room in the course of the day. It is often impractical to move anesthesia carts to follow a particular anesthesiologist, so medications must be transferred to the cart in another operating room via box or bag and then that anesthesia cart must be locked. The transport of that bag or plastic container is not secure from cart to cart and could be intercepted. A smart container that securely transports medications avoids this vulnerability and provides additional accountability.

Another advantage of a portable smart container is that anesthesia carts need to be unlocked while taking care of patients. There are non-controlled medications that may be needed within seconds of a crisis. Unlocking the anesthesia cart means fumbling with keys or an unlocking mechanism that uses precious time that the patient may not have. An unlocked anesthesia cart does not secure the controlled medications that are needed in the routine care of a patient. It would be unusual for the emergent need of controlled substances so a few seconds delay in delivery of those medications does not pose a risk to patient care.

A smart container secures the controlled medications in transport from room to room and allows the anesthesia carts to be unlocked for emergent needs. The secure smart container removes the temptation of opportunistic diversion of medications by a nurse, physician, medical device representative or observer.

This smart container's portability presents a vulnerability that stationary methods do not have. Given an unobserved opportunity, removing a normal container from the facility would not be difficult. In this embodiment, the smart container will have wireless access to the cloud via WiFi protocols, Bluetooth, cellular, GPS, LORA or other radio transmitted protocols to determine the location and transmit the location to a server, smart phone or other computer. Removal of the device or attempted removal noted by uncharacteristic location changes or unusual removal of controlled substances outside the norm of a practice of an anesthesiology practice or routine can trigger an alert to interested parties to log its location, motion and time of the unauthorized movements.

The ability to locate itself provides another benefit in the discouragement of diversion. The smart container will only be allowed to open in authorized locations or authorized perimeters. Only opening the smart container in operating rooms, GI suites and locations where narcotics are distributed to patients while preventing the opening of smart container in hallways, bathrooms, closets removes the opportunity to swap vials in a diversion attempt. Logging of opening of the container in various locations, enforces the accountability of medication usage and distribution.

Limiting who can open this smart container will be constrained by the use of RFID card or smart phone application and/or biometrics. Biometric measures such as fingerprints, visual recognition of a given individual would certainly be entertained with other embodiments but the use of masks and gloves in an operating room makes those features less preferable to an RFID card or smart phone with Bluetooth, NFC or other local radio secure communications to authorize opening or locking of the smart container. Logging of authorized access to the container will include such data as location, time and method of access. Logging of this data improves the chain of custody of the medication usage.

The embodiment of a smart container can further include motion sensors, weight sensors and RFID readers.

This embodiment of a smart container requires intermittent and continuous power. Intermittent power to the electronics can be provided with an onboard battery of sufficient storage to provide communications to the network to locate, access and communicate the activities of the smart container. Continuous or additional power will be needed to charge the onboard battery. That will come from a base station or a cart as shown in FIG. 6 where the device can be charged overnight. A secondary power station can be located in the operating room to charge or power the device. These secondary stations can reinforce the location requirements by delivering power and a locking mechanism in various embodiments.

In some embodiments, the system can be a client device having one or more computer storage mediums containing computer instructions enabling secure access, storage, transport, and tracking of electronically tagged objects, one or more processors operationally coupled to the one or more computer storage mediums where the one or more processors perform the operations described above.

Figure 5:
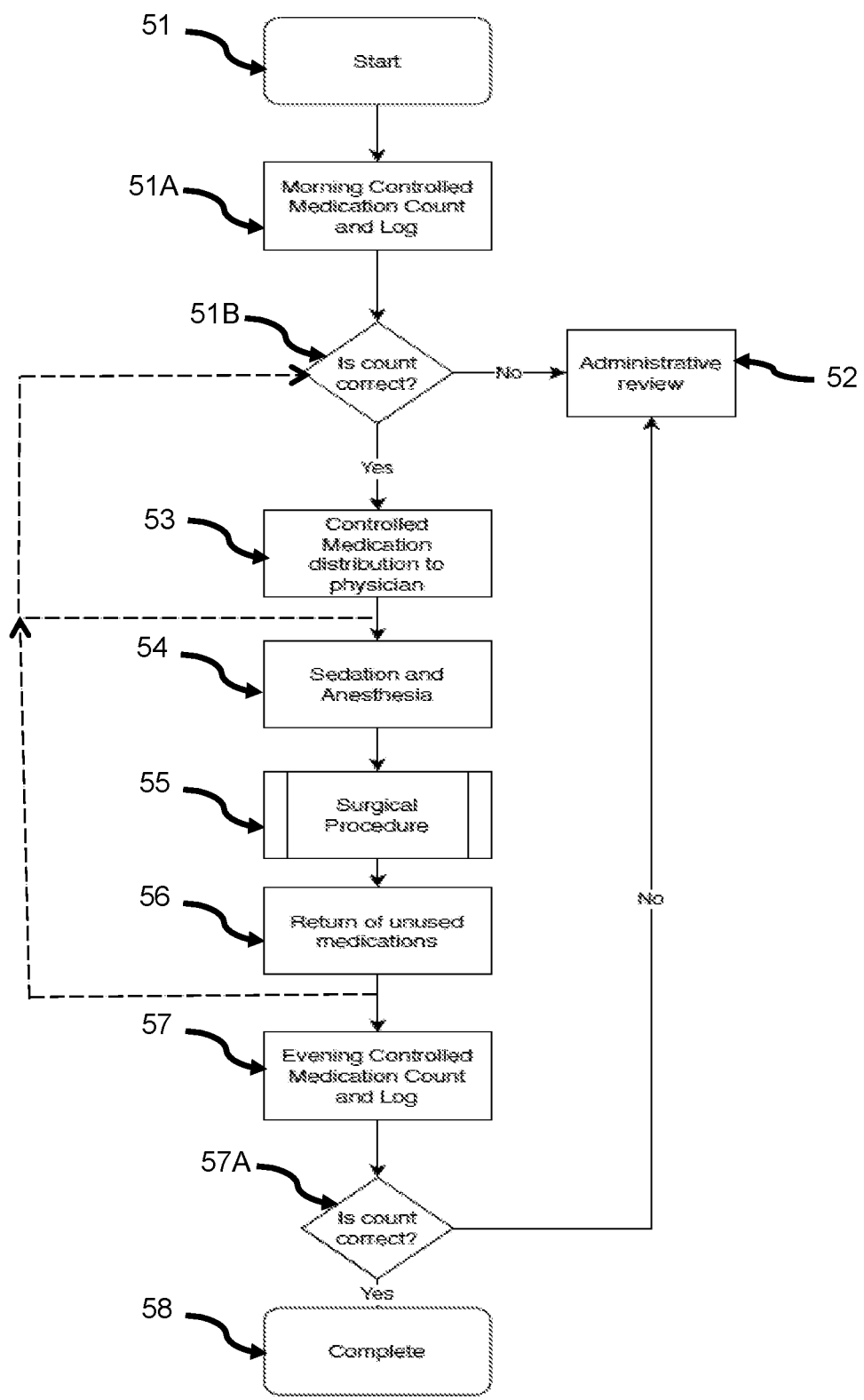
FIG. 5 is a flow chart representing a method of tracking using the system of FIG. 1 in accordance with the embodiments.

In some embodiments, the system can further include a computer-storage media coupled to a processor (or processors) and computer-executable instructions embodied in the computer-storage media that, when executed by one or more computing devices, perform a method that perform any number of steps such as performing the method described with respect to FIG. 5.

Various embodiments of the present disclosure can be implemented on an information processing system. The information processing system is capable of implementing and/or performing any of the functionality set forth above. Any suitably configured processing system can be used as the information processing system in embodiments of the present disclosure. The information processing system is operational with numerous other general purpose or special purpose computing system environments, networks, or configurations. Examples of well-known computing systems, environments, and/or configurations that may be suitable for use with the information processing system include, but are not limited to, personal computer systems, server computer systems, thin clients, hand-held or laptop devices, notebook computing devices, multiprocessor systems, mobile devices, microprocessor-based systems, set top boxes, programmable consumer electronics, network PCs, minicomputer systems, mainframe computer systems, Internet-enabled television, and distributed cloud computing environments that include any of the above systems or devices, and the like. As noted previously, the data processing can be any number of data processing techniques suited for the controlled access or authentication, tracking, logging or counting or electronically tagged objects, logging or tracking of location of a lockbox in any setting or environment where objects need to be tracked and logged including setting such as medical facilities generally.

For example, a user with a mobile device may be in communication with a server configured to implement the system using the aforementioned elements, according to an embodiment of the present disclosure. The mobile device can be, for example, a multi-modal wireless communication device, such as a "smart" phone, configured to store and execute mobile device applications ("apps"). Such a wireless communication device communicates with a wireless voice or data network using suitable wireless communications protocols.

The system may include, inter alia, various hardware components such as processing circuitry executing modules that may be described in the general context of computer system-executable instructions, such as program modules, being executed by the system. Generally, program modules can include routines, programs, objects, components, logic, data structures, and so on that perform particular tasks or implement particular abstract data types. The modules may be practiced in various computing environments such as conventional and distributed cloud computing environments where tasks are performed by remote processing devices that are linked through a communications network. In a distributed cloud computing environment, program modules may be located in both local and remote computer system storage media including memory storage devices. Program modules generally carry out the functions and/or methodologies of embodiments of the present disclosure, as described above.

In some embodiments, a system includes at least one memory and at least one or more processor of a computer system communicatively coupled to the at least one memory. The at least one processor can be configured to perform a method including methods described above.

According to yet another embodiment of the present disclosure, a computer readable storage medium comprises computer instructions which, responsive to being executed by one or more processors, cause the one or more processors to perform operations as described in the methods or systems above or elsewhere herein.

As shown in FIG. 7, an information processing system 101 of a system 200 can be communicatively coupled with the data processing module 150 and a group of client or other devices, or coupled to a presentation device for display at any location at a terminal or server location. According to this example, at least one processor 102, responsive to executing instructions 107, performs operations to communicate with the processing module 150 via a bus architecture 208, as shown. The at least one processor 102 is communicatively coupled with main memory 104, persistent memory 106, and a computer readable medium 120. The processor 102 is communicatively coupled with an Analysis & Data Storage 115 that, according to various implementations, can maintain stored information used by, for example, the data processing module 150 and more generally used by the information processing system 200. The data processing module 150 can be coupled to one or more sensors 152 as needed. Such sensors can be barcode scanners, fingerprint readers, proximity sensors, microphones, cameras, video cameras, location sensors, motion detectors, scales, biometric reading devices (e.g., iris scanners, facial recognition scanners, voice detection devices) and other devices as contemplated herein. Optionally, this stored information can be received from the client or other devices. For example, this stored information can be received periodically from the client devices and updated or processed over time in the Analysis & Data Storage 115. Additionally, according to another example, a history log can be maintained or stored in the Analysis & Data Storage 115 of the information processed over time. The data processing module 150, and the information processing system 200, can use the information from the history log such as in the analysis process and in making decisions related to a particular user's access or for logging electronically tagged objects according to a database of best practices for a particular procedure or procedures.

The computer readable medium 120, according to the present example, can be communicatively coupled with a reader/writer device (not shown) that is communicatively coupled via the bus architecture 208 with the at least one processor 102. The instructions 107, which can include instructions, configuration parameters, and data, may be stored in the computer readable medium 120, the main memory 104, the persistent memory 106, and in the processor's internal memory such as cache memory and registers, as shown.

The information processing system 200 includes a user interface (or interfaces) 110 that comprises a user output interface 112 and user input interface 114. Examples of elements of the user output interface 112 can include a display, a speaker, one or more indicator lights, one or more transducers that generate audible indicators, and a haptic signal generator or any of the interfaces illustrated or discussed with respect to the figures or elsewhere in the application. Examples of elements of the user input interface 114 can include a keyboard, a keypad, a mouse, a track pad, a touch screen, a touch pad, a microphone that receives audio signals, a camera, a video camera, a CT-Scanner, or any other scanner that scans images. Some user inputs can be sensors or vice-versa. The received audio signals or scanned images, for example, can be converted to electronic digital representations and stored in memory, and optionally can be used with corresponding voice or image recognition software executed by the processor 102 to receive user input data and commands, or to receive test data for example. The voice recognition software can be used to enter or check off items on a checklist and further provide data or text entry allowing the practitioner to enter notes as needed.

A network interface device 116 is communicatively coupled with the at least one processor 102 and provides a communication interface for the information processing system 100 to communicate via one or more networks 108. The networks 108 can include wired and wireless networks, and can be any of local area networks, wide area networks, or a combination of such networks. For example, wide area networks including the internet and the web can intercommunicate the information processing system 100 with other one or more information processing systems that may be locally, or remotely, located relative to the information processing system 100. It should be noted that mobile communications devices, such as mobile phones, Smart phones, tablet computers, lap top computers, and the like, which are capable of at least one of wired and/or wireless communication, are also examples of information processing systems within the scope of the present disclosure. The network interface device 116 can provide a communication interface for the information processing system 100 to access the at least one database 117 according to various embodiments of the disclosure.

The instructions 107, according to the present example, can include instructions for monitoring, instructions for analyzing, instructions for retrieving and sending information and related configuration parameters and data. It should be noted that any portion of the instructions 107 can be stored in a centralized information processing system or can be stored in a distributed information processing system, i.e., with portions of the system distributed and communicatively coupled together over one or more communication links or networks.

FIGS. 1-7 illustrate examples of systems, methods or process flows, according to various embodiments of the present disclosure, which can operate in conjunction with the information processing system 200 of FIG. 7.

The invention claimed is:

1. A system for holding, transporting, and tracking electronically tagged objects maintained in a portable carrier housing, comprising:
 a locking mechanism for enabling limited authorized access to the portable carrier housing using a proximity sensor recognizing an identity code of an authorized user where the portable carrier housing goes to an unlocked status when the proximity sensor detects the identity code of the authorized user and returns to a locked status when the proximity sensor fails to detect the identity code of the authorized user;

a location tracker coupled the portable carrier for detecting the location of the portable carrier at least when the locking mechanism changes status from the locked status to the unlocked status or when the locking mechanism changes from the unlocked status to the locked status;

an inventory logger registering placement and removal of the electronically tagged objects within and out of the portable carrier housing, registering the location of the portable carrier housing at a time of placement or removal of the electronically tagged object, and registering the identity code of the authorized user within proximity of the proximity sensor causing the locking mechanism to provide limited authorized access;

a transmitter for uploading data from the inventory logger to a database; and a receiver for at least receiving instructions for remotely locking the portable carrier housing when detecting an attempted unauthorized access or detecting a condition indicative of unauthorized access wherein the attempted unauthorized access or the condition indicative of unauthorized access is an attempted access outside a predefined dispensing schedule or outside a predefined geographic area.

2. The system of claim 1, wherein the proximity sensor uses a Radio Frequency Identification (RFID) tag or a Near Field Communication (NFC) device.

3. The system of claim 1, wherein the system determines the attempted unauthorized access or the condition indicative of unauthorized access using machine learning by using data including typical dispensing schedules or typical geographic areas for dispensing.

4. The system of claim 1, wherein the electronically tagged objects use Radio Frequency Identification (RFID) tags and barcodes.

5. The system of claim 1, wherein the electronically tagged objects are vials of medicine or syringes.

6. The system of claim 1, wherein the electronically tagged objects are one or more selected among keys, firearms, ammunition, or medicine.

7. The system of claim 1, wherein the locking mechanism is a biometric access system selected among a fingerprint reader, a facial recognition reader, a iris scanner, or a voice recognition reader.

8. The system of claim 1, wherein the identity code is stored in a mobile phone of the authorized user.

9. The system of claim 1, wherein the system further includes a processor configured to acknowledge the receipt of a temporary grant access code from the authorized user to a third party enabling temporary access by the third party to the portable carrier housing.

10. The system of claim 1, wherein the portable carrier housing further comprises a vial registration system using slots within the portable carrier housing and wherein the vial registration system uses one or more among magnetism, barcodes, or mechanical registration to register the placement or removal of vials within the portable carrier housing.

11. The system of claim 1, wherein the portable carrier housing further comprises a vial registration system using slots within the portable carrier housing and wherein the vial registration system uses one or more among magnetism, barcodes, or mechanical registration to register the placement or removal of vials within a particular slot of the portable carrier housing.

12. The system of 1, wherein the portable carrier housing further includes at least one scale that automatically weighs the electronically tagged object upon insertion into the portable carrier housing.

13. The system of claim 1, wherein the location tracker comprises one or more among a GPS device, a beacon reading device, a camera, or any combination thereof.

14. The system of claim 1, wherein the system registers transfers of electronically tagged objects from a main storage site to the portable carrier housing.

15. The system of claim 1, wherein the system registers inventory data a first time in a day when electronically tagged objects are transferred from a main storage site to the portable carrier housing and registers inventory data a second time in the day when portable carrier housing is returned to the main storage site.

16. The system of claim 1, wherein the system further comprises a cart for carrying the portable carrier housing and wherein the cart comprises a power-charging source for charging rechargeable batteries stored within the portable carrier housing.

17. The system of claim 1, wherein the portable carrier housing comprises a modular carrying component enabling different configurations for carrying different shapes or amounts of the electronically tagged objects.

18. A system for holding, transporting, and tracking electronically tagged medicine containers maintained in a portable carrier housing, comprising:

a locking mechanism for enabling limited authorized access to the portable carrier housing using an identity code representative of an authorized user;

a location tracker coupled the portable carrier for enabling limited authorized access to the portable carrier housing using an identity code representative of an authorized user an inventory logger registering placement and removal of the electronically tagged medicines within and out of the portable carrier housing, registering the location of the portable carrier housing at a time of placement or removal of the electronically tagged medicine, and registering the identity code of the authorized user when placing or removing the electronically tagged medicines;

a transmitter for uploading data from the inventory logger to a database;

a receiver for at least receiving instructions for remotely locking the portable carrier housing when detecting an attempted unauthorized access or detecting a condition indicative of an attempted authorized access and wherein the attempted unauthorized access or the condition indicative of unauthorized access is an attempted access outside a predefined dispensing schedule or a predefined geographic area.

19. The system of claim 18, wherein the locking mechanism uses a proximity sensor and wherein the portable carrier housing goes to an unlocked status when the proximity sensor detects the identity code of the authorized user and returns to a locked status when the proximity sensor fails to detect the identity code of the authorized user.

20. A system for holding, transporting, and tracking electronically tagged medicine containers maintained in a portable carrier housing, comprising:

a locking mechanism for locking and unlocking access to the portable carrier housing;

a transceiver;

a memory having computer instructions stored therein;

one or more processors operatively coupled to the memory, transceiver, and locking mechanism, wherein the one or more processors when executing the computer instructions, performs the functions comprising:
enabling limited authorized access to the portable carrier housing using an identity code representative of an authorized user using the locking mechanism;
enabling limited authorized access to the portable carrier housing using an identity code representative of an authorized user using a location tracking device;
registering placement and removal of the electronically tagged medicines within and out of the portable carrier housing, registering the location of the portable carrier housing at a time of placement or removal of the electronically tagged medicine, and registering the identity code of the authorized user when placing or removing the electronically tagged medicines using an inventory logger;
uploading data using the transceiver from the inventory logger to a database; and
receiving instructions using the transceiver for remotely locking the portable carrier housing when detecting an attempted unauthorized access or detecting a condition indicative of an attempted authorized access wherein the attempted unauthorized access or the condition indicative of unauthorized access is an attempted access outside a predefined dispensing schedule or a predefined geographic area.

* * * * *